United States Patent [19]

Karbosky et al.

[11] 4,331,461
[45] May 25, 1982

[54] CRYOGENIC SEPARATION OF LEAN AND RICH GAS STREAMS

[75] Inventors: Joseph T. Karbosky; Dunn M. Bailey, both of Bartlesville, Okla.

[73] Assignee: Phillips Petroleum Company, Bartlesville, Okla.

[21] Appl. No.: 885,402

[22] Filed: Mar. 10, 1978

[51] Int. Cl.³ .................................................. F25J 3/02
[52] U.S. Cl. ............................................ 62/28; 62/23; 62/38
[58] Field of Search ................ 62/28, 27, 23, 26, 24, 62/31, 38, 39

[56] References Cited

U.S. PATENT DOCUMENTS

| | | | |
|---|---|---|---|
| 2,487,147 | 11/1949 | Latchum, Jr. | 62/28 |
| 2,940,271 | 6/1960 | Jackson | 62/23 |
| 3,218,816 | 11/1965 | Grenier | 62/28 |
| 3,274,787 | 9/1966 | Grenier et al. | 62/23 |
| 4,002,042 | 1/1977 | Pryor et al. | 62/28 |

*Primary Examiner*—Norman Yudkoff

[57] ABSTRACT

A process for simultaneously, cryogenically separating natural gas liquids from a lean natural gas stream and a rich natural gas stream; including, compressing the lean gas feed, cooling the compressed lean gas feed, separating the cooled lean gas feed to form a vapor phase and a liquid phase, expanding the vapor phase lean gas feed, separating the expanded vapor phase lean gas feed to form a second vapor phase and a second liquid phase, fractionating the second vapor phase lean gas feed to form a methane-enriched, low pressure bottoms fraction and a nitrogen-enriched, high pressure overhead fraction, flashing a portion of the methane-enriched bottoms fraction and passing the same in countercurrent, indirect heat exchange with the nitrogen-enriched overhead fraction, to cool the same and produce a vapor phase nitrogen-enriched product and a liquid phase reflux for the fractionator, passing the remainder of the methane-enriched bottoms fraction, the flashed methane-enriched bottoms fraction and the vapor phase nitrogen-enriched fraction in countercurrent heat exchange with the lean gas feed, compressing the rich gas feed, cooling the compressed rich gas feed, fractionating the cooled rich gas feed and the liquid phases separated from the lean gas feed to form a methane-enriched overhead fraction and a natural gas liquids bottoms product and combining the methane-enriched overhead with a portion of the methane-enriched bottoms product from the lean gas feed, prior to the passage of the latter in heat exchange with the lean gas feed. The methane-enriched streams are combined, following their use as heat exchange media, to form a pipeline quality natural gas product and the nitrogen-enriched vapor phase can be utilized as a low BTU fuel gas for the plant.

39 Claims, 1 Drawing Figure

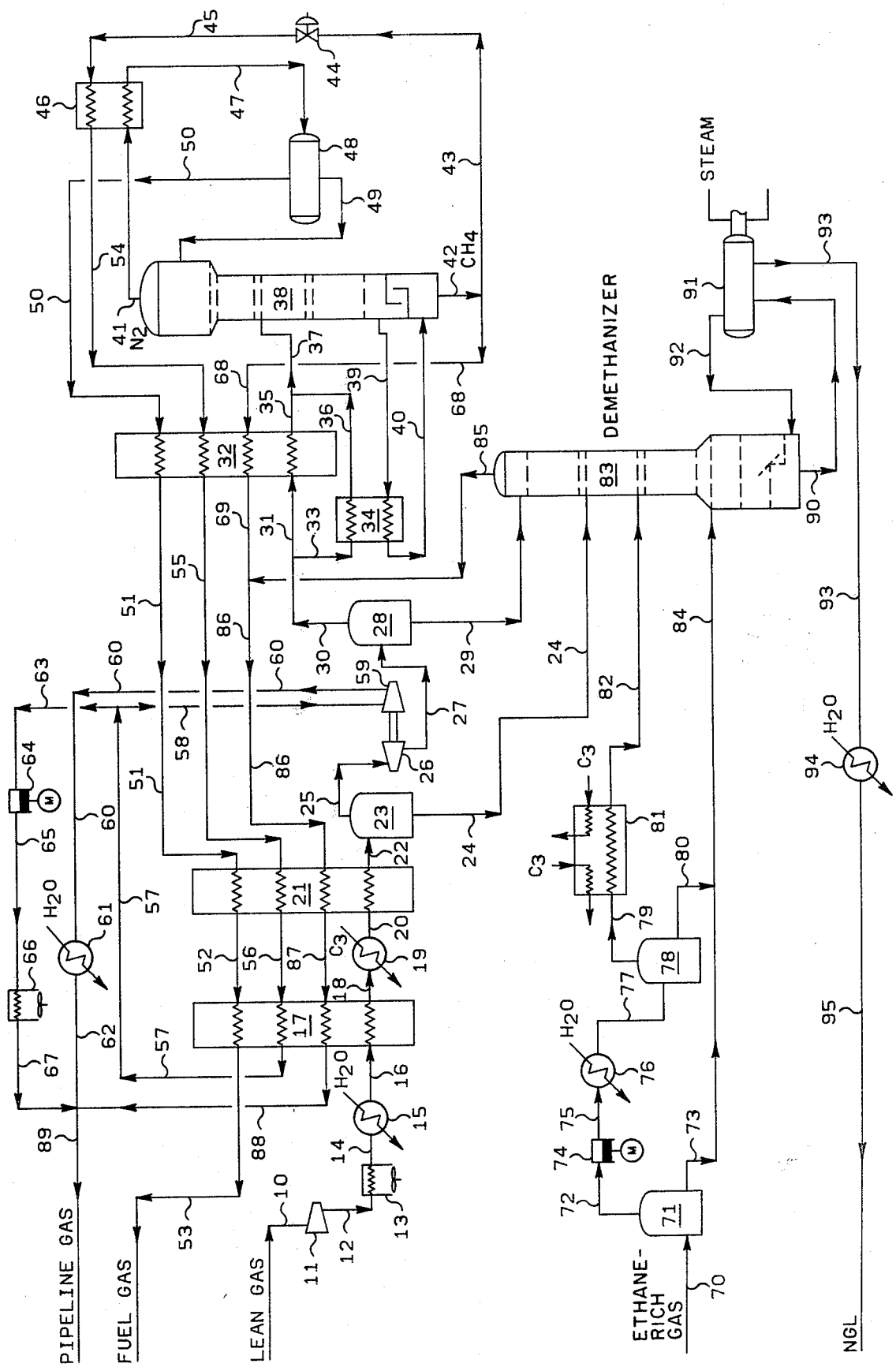

CRYOGENIC SEPARATION OF LEAN AND RICH GAS STREAMS

SUMMARY OF THE INVENTION

The present invention relates to a process for cryogenically, simultaneously separating a lean natural gas, containing significant volumes of nitrogen, and a rich natural gas to form a nitrogen-enriched gas product, a methane-enriched gas product and a natural gas liquids product.

It is known in the prior art that lean natural gas streams, containing nitrogen and very small amounts of ethane and heavier hydrocarbons, can be separated cryogenically to produce a nitrogen-enriched gas and a methane-enriched gas as well as a small amount of natural gas liquids. In such processes, the lean gas feed is pressurized and cooled, by various refrigerants (such as propane, ethylene, nitrogen, etc.) to temperatures sufficiently low to liquefy the lean gas stream. Thereafter, the liquefied lean gas is fractionated by flashing a nitrogen-enriched gas stream therefrom to leave a methane-enriched liquid product, containing the natural gas liquids, as a bottoms fraction. The methane-enriched liquid product is then further processed to flash off a methane-enriched gas product and leave a natural gas liquids product as a bottoms fraction.

This process as well as other similar processes have a number of disadvantages. For example, the well known cascade-type refrigeration systems require a heavy outlay of equipment, leading to high initial plant costs and high operating costs. Additionally, the cascade-type system requires facilities to purify, replenish and store the refrigerants and there is usually no significant recovery of the cost of such cooling.

It is also known, in the prior art, that rich natural gas streams, containing predominant volumes of $C_2$ plus hydrocarbons, can be cryogenically separated to produce a methane-enriched natural gas and a natural gas liquids product. Such processes also require substantial expenditures for the installation of equipment and the processing and supplying of various refrigerants (such propane, ethylene, nitrogen, etc.). In addition, such plants generally provide no significant means for recovering the cost of such cooling.

It is therefore an object of the present invention to provide a solution to the above-mentioned problems. Another object of the present invention is to provide an improved process for the simultaneous, cryogenic separation of a lean natural gas stream, containing significant amounts of nitrogen, and a rich natural gas stream. Yet another object of the present invention is to provide a process for the simultaneous, cryogenic separation of a lean gas stream, containing significant amounts of nitrogen, and a rich gas stream while utilizing little external refrigeration. Yet another object of the present invention is to provide a process for the simultaneous, cryogenic separation of a lean gas stream, containing significant amounts of nitrogen, and a rich gas stream to produce a methane-enriched, pipeline quality natural gas, a nitrogen-enriched plant fuel gas and natural gas liquids. Still another object of the present invention is to provide a process for the simultaneous, cryogenic separation of a lean gas stream, containing significant amounts of nitrogen, and a rich gas stream, wherein only lean gas, essentially free of natural gas liquids, is fractionated for nitrogen separation and only the rich gas and natural gas liquids, separated from the lean gas, are fractionated to separate natural gas liquids. Another and further object of the present invention is to provide a process for the simultaneous, cryogenic separation of a lean gas stream, containing significant amounts of nitrogen, and a rich gas stream, wherein reflux for a lean gas fractionator and reflux for a rich gas fractionator are produced internally, without the need for separate, external facilities.

These and other objects and advantages of the present invention will be apparent from the following detailed description.

BRIEF DESCRIPTION OF THE DRAWING

The single FIGURE of the drawing shows a simplified flow diagram of the process of the present invention.

DETAILED DESCRIPTION

In accordance with the present invention a lean natural gas stream, containing significant amounts of nitrogen, and a rich natural gas stream, predominating in $C_2$ plus hydrocarbons, are simultaneously, cryogenically fractionated to produce a pipeline quality, methane-enriched gas product, a nitrogen-enriched, low BTU plant fuel gas product and a natural gas liquids product.

By way of specific examples, the lean gas feed is compressed, to about 740 to 760 psia, and cooled, by external refrigeration and heat exchange with cooled exiting gas streams, to about $-90°$ to $-100°$ F. The cooled, lean gas feed is phase-separated to recover an uncondensed vapor which is expanded to about 400 to 450 psia, and further separated in a second stage, to produce a vapor phase and a liquid phase. A portion of the vapor phase is utilized in indirect, countercurrent heat exchange with reboiler materials from a nitrogen fractionation column while the remainder of the vapor phase is further cooled to about $-165°$ to $-180°$ F. and fed to a nitrogen fractionation column. Overhead vapors from the nitrogen fractionation column are partially condensed by flashing a first portion of the nitrogen fractionation column bottoms and indirectly, heat exchanging the overhead vapors with the flashed bottoms in a reflux condenser. Condensate from the cooled overhead vapors is returned to the column, as reflux, and the vapor phase of the cooled overhead vapors is countercurrently, heat exchanged with the lean gas feed in three stages. Following their use as a refrigerant, the vapors separated from the overhead of the nitrogen fractionation column are available as a low BTU, fuel gas for plant use.

The rich gas feed passes through a phase separator, near ambient temperature, and the vapor therefrom is compressed to about 425 psia, cooled to about 90° F. and again phase separated. The separated vapor from the second phase separator is cooled and partially condensed by two stages of propane refrigeration to about 0° F. and is thereafter fed to a demethanizer fractionation column together with natural gas liquids separated in the two-stage phase separation of the lean gas feed. Previously condensed and separated liquids from the rich gas feed are also introduced to the demethanizer fractionator column at a lower point in the column. Demethanizer fractionation column bottoms are cooled to yield a natural gas liquids product.

The remainder or second portion of the bottoms product of the nitrogen fractionation column is combined with the overhead vapor from the demethanizer fractionation column and heat exchanged in countercurrent fashion with the lean gas feed in a first two-stage heat exchanger. The previously discussed first portion of the bottoms product of the nitrogen fractionation column, which was flashed to low pressure for refrigeration purposes, is recompressed to about 231 psia, upon exiting the heat exchanger train, and is blended with the combined demethanizer overhead and second portion of the nitrogen fractionation column bottoms, after exiting the heat exchange train, and is recovered as a pipeline quality gas product.

This specific example will now be explained by reference to the drawing. It is to be understood that many valves, pumps, control instruments and other conventional equipment have been eliminated from the drawing for the sake of clarity and brevity. For convenience, and not by way of limitation, the invention is illustrated and specifically described with reference to the separation of a lean gas stream, containing significant nitrogen, and a rich gas stream, containing predominant amounts of $C_2$ plus hydrocarbons, both obtained from a helium recovery plant. However, it is obvious that other essentially lean and essentially rich gas streams may be utilized in the present process. The initial temperatures and pressures as well as the components of the feed gas streams may vary widely without departing from the present invention. Accordingly, a lean gas stream as used herein, is normally meant to include any lean gas predominating in methane and containing significant volumes of nitrogen and relatively small amounts of $C_2$ and higher hydrocarbons. On the other hand, a rich gas stream, when referred to herein, is meant to include any gas stream containing little or no nitrogen, small amounts of methane and predominating in ethane and higher hydrocarbons.

It should also be understood that the representative temperatures and pressures set forth herein, with relation to the description of the drawing and the examples, are illustrative only and are not to be considered as limiting. The particular temperatures and pressures utilized in a particular separation will be dependent upon the nature and composition of the feedstreams, upon the particular heat exchange surface areas available and upon the initial temperatures and pressures of the feedstreams.

Lean gas is fed to the system through line 10. The lean gas feed is compressed in turbo-compressor 11 and discharged through line 12. The compressed gas is cooled by means of air fin cooler 13 and is fed through line 14 to water cooler 15. The cooled gas is passed through line 16 to first bank 17 of a two-stage heat exchanger. Gas from heat exchanger 17 passes through line 18 to propane chiller and evaporator 19. Gas from chiller 19 passes through line 20 to second bank 21 of the two-stage heat exchanger. The cooled gas is then passed through line 22 to lean gas separator 23. In separator 23, the gas is separated into a condensed liquid stream 24 and an uncondensed vapor stream 25. The uncondensed vapor passing through line 25 is expanded in expander section 26 a of turbo-expander and -compressor. The expanded, partially condensed vapor is discharged through line 27 to a second separator 28. Separator 28 produces a second condensed liquid stream 29 and a second uncondensed vapor stream 30. A first portion of vapor stream 30 is passed through line 31 to a second lean gas heat exchanger 32. A second portion of uncondensed, vapor stream 30 is passed through line 33 to nitrogen column (hereinafter referred to) reboiler 34. Reboiler 34 is shown to be a separate unit in the drawing, as a matter of convenience. However, reboiler 34 is actually in the base of the hereinafter mentioned nitrogen separation column. Cooled lean gas from heat exchanger 32 is passed through line 35 and lean gas from reboiler 34 is passed through line 36. The two gas streams from lines 35 and 36 are combined in line 37 and fed to nitrogen separation column 38. Reboiling medium from nitrogen column 38 is introduced to reboiler 34 through line 39 and is returned to nitrogen column 38 through line 40.

Nitrogen separation column 38 produces an overhead fraction or nitrogen-enriched gas stream through line 41 and a bottoms fraction or methane-enriched residue through line 42. A portion of the methane-enriched residue from line 42 is passed through line 43 to an expansion valve 44, or similar expansion means, wherein this portion of the methane-enriched residue is flashed and passed through line 45. The flashed, methane-enriched residue from line 45 is passed through reflux condenser 46, in indirect heat exchange with the nitrogen-enriched gas stream from line 41. The nitrogen-enriched gas stream from condenser 46 passes through line 47 to reflux accumulator 48. A reflux stream from accumulator 48 is passed through line 49 to nitrogen separator column 38. Vapor from accumulator 48 is discharged through line 50 and thence in countercurrent exchange with lean gas feed in exchanger 32. From exchanger 32 the nitrogen-enriched gas stream passes through line 51 to the second bank 21 of the two-stage heat exchanger in countercurrent heat exchange with lean feed gas. The nitrogen-enriched gas stream is then passed through line 52 to the first bank 17 of the two-stage heat exchanger, wherein it flows countercurrently to the lean feed gas. From the second bank 17 of the two-stage heat exchanger, the nitrogen-enriched gas stream is passed through line 53, from which it may be accumulated in storage or utilized as a fuel gas for plant processes or other uses, where a gas high in nitrogen can be tolerated. The methane-enriched residue, which is flashed through condenser 46, then passes through line 54, to heat exchanger 32, through line 55 to second bank 21 of the two-stage heat exchanger, through line 56 and to the first bank 17 of the two-stage heat exchanger, all in countercurrent heat exchange with lean feed gas. From first bank 17 of the two-stage heat exchanger, the methane-enriched residue passes to line 57. A major portion of the methane-enriched residue from line 57 is passed through line 58 to compressor section 59 of the turbo-expander and -compressor. The compressed methane-enriched residue is discharged through line 60 to water cooler 61. Cooled gas from water cooler 61 is discharged through line 62. The gas passing through line 62 is a methane-enriched gas suitable for use as a domestic pipeline gas or the like. A second portion of the methane-enriched residue passing through line 57 is passed through line 63 to compressor 64. The compressed gas is discharged through line 65 to air fin cooler 66. Cooled gas from cooler 66 is thereafter discharged through line 67 and is added to the pipeline gas passing through line 62. Splitting the gas stream from line 57, and separately compressing and cooling the two streams, provides greater flexibility for the treatment of lean gas feeds of differing compositions.

A second portion of the methane-enriched residue from nitrogen separation column 38 is passed through line 68 and thence in countercurrent heat exchange with the lean feed gas in heat exchanger 32. From heat exchanger 32 the methane-enriched residue passes to line 69.

A rich gas stream, from a suitable source and containing substantially no impurities, such as nitrogen, but having predominant amounts of ethane and higher boiling hydrocarbons, is fed to the system through line 70. The rich gas from line 70 is passed to a phase separator 71, wherein it is separated into an uncondensed vapor fraction, which is discharged through line 72, and a condensed liquid fraction which is discharged through line 73. The vapor fraction from line 72 is compressed in compressor 74 and discharged through line 75. The compressed vapors from line 75 are cooled in water cooler 76. The cooled vapors from cooler 76 pass through line 77 to a second phase separator 78. In phase separator 78, rich feed gas is again separated into an uncondensed vapor fraction, which is discharged through line 79, and a condensed liquid fraction, which is discharged through line 80. The uncondensed vapor from line 79 is introduced into cooler 81, wherein it is countercurrently cooled with propane in two stages. The cooled rich gas from cooler 81 passes through line 82 and is introduced, at an intermediate point, into demethanizer column 83. The condensed liquids from lines 73 and 80 are combined in line 84 and fed to demethanizer column 83 at a low point therein. Demethanizer column 83 separates the feed materials from lines 24, 29, 82 and 84 into an overhead vapor stream 85 and a bottoms liquid stream 90. It should be noted at this point that the liquid fractions passing through lines 24 and 29 serve as an effective reflux for demethanizer 83, thus eliminating the need for separate external reflux generating equipment. Vapor stream 85 is combined with methane-enriched residue from nitrogen column 38, which is passing through line 69, and is introduced into line 86. The gas in line 86 is passed, countercurrently to the lean gas feed, through the second bank 21 of the two-stage heat exchanger, thence through line 87 to the first bank 17 of the two-stage heat exchanger, again in countercurrent heat exchange with lean gas feed, and, finally, through line 88. The gas in line 88 is also a suitable pipeline gas, rich in methane, and, therefore, is combined with pipeline gas passing through lines 62 and 67 and is discharged to the pipeline through line 89. The liquid bottoms product from demethanizer column 83 is discharged through line 90 to demethanizer column reboiler 91. Vapors from reboiler 91 are reintroduced into the bottom of demethanizer column 83 through line 92. Natural gas liquids from reboiler 91 are discharged through line 93 to water cooler 94. The natural gas liquid product is then discharged from water cooler 94 through line 95.

It is to be observed, from the above description, that the process of the present invention provides for the multiple use of a single demethanizer fractionation column to fractionate rich gas, together with liquids condensed at low temperature from a lean gas stream and that each of the feedstreams to the demethanizer column can be introduced at a level in the column which is appropriate to its temperature and composition.

It should also be noted that the second stage lean gas separator, following the expander, operates at approximately the pressure of the demethanizer fractionation column. Consequently, the liquid from this separator contains more than about 55 percent of the remaining ethane in the lean gas and provides adequate refluxing action for the demethanizer column, so that separate reflux generating facilities are not required.

By flashing a sufficient amount of the bottoms product of the nitrogen fractionation column to generate reflux for the nitrogen column, adequate reflux is provided for the fractionation column without external facilities. The remainder of the nitrogen column overhead is heat exchanged at high pressure to supply a substantial portion of the refrigeration requirements for the lean gas feed. In addition, the power requirements for recompression of the low pressure methane-enriched gas, from the bottoms product of the nitrogen column can be met by the power generated by the lean gas feed expander.

It should also be noted that the nitrogen-enriched gas stream can be utilized to supply an internal plant fuel for operation of various compressors, pumps and the like.

The following table sets forth the compositions, temperatures and pressures of fluid streams at appropriate points in the plant, referring specifically to the number of the equipment connecting lines of the drawing. The data given are for typical lean and rich gas streams from two helium recovery plants, designated as plants A and B, respectively. For convenience, negative temperatures are shown in parenthesis.

| Line No. | Compositions (Mol %) - Temperatures (°F.) - Pressures (psia) | | | | | | | | | | | | | | |
|---|---|---|---|---|---|---|---|---|---|---|---|---|---|---|---|
| | $N_2$ | | $C_1$ | | $C_2$ | | $C_3$ | | $C_4$ | | $C_{5+}$ | | Temp. | | Press. |
| | A | B | A | B | A | B | A | B | A | B | A | B | A | B | A | B |
| 10(a) | 11.76 | 9.71 | 82.15 | 82.51 | 4.99 | 6.31 | 0.95 | 1.35 | 0.13 | 0.10 | 0.03 | 0.01 | 90 | 90 | 215 | 215 |
| 24 | 4.14 | 3.64 | 70.74 | 71.03 | 16.99 | 17.97 | 6.57 | 6.62 | 1.33 | 0.65 | 0.23 | 0.10 | (95) | (92) | 740 | 740 |
| 25 | 12.41 | 10.66 | 83.11 | 84.31 | 3.98 | 4.49 | 0.47 | 0.52 | 0.03 | 0.02 | 0.00 | 0.00 | " | " | " | " |
| 29 | 2.68 | 2.22 | 70.95 | 69.31 | 21.86 | 23.76 | 4.18 | 4.53 | 0.32 | 0.18 | 0.01 | 0.00 | (134) | (131) | 410 | 410 |
| 30 | 13.49 | 11.63 | 84.47 | 86.02 | 1.98 | 2.28 | 0.06 | 0.07 | 0.00 | 0.00 | 0.00 | 0.00 | " | " | " | " |
| 41 | 6.33 | 4.32 | 91.38 | 93.01 | 2.24 | 2.60 | 0.06 | 0.08 | 0.00 | 0.00 | 0.00 | 0.00 | (207) | (203) | 65 | 65 |
| 42 | " | " | " | " | " | " | " | " | " | " | " | " | (186) | (181) | 230 | 230 |
| 49 | 25.51 | 21.89 | 74.49 | 78.11 | 0.00 | 0.00 | 0.00 | 0.00 | 0.00 | 0.00 | 0.00 | 0.00 | (219) | (214) | 225 | 225 |
| 50 | 69.97 | 64.99 | 30.03 | 35.01 | 0.00 | 0.00 | 0.00 | 0.00 | 0.00 | 0.00 | 0.00 | 0.00 | " | " | " | " |
| 53(c) | " | " | " | " | " | " | " | " | " | " | " | " | 84 | 84 | 218 | 218 |
| 68 | 6.33 | 4.32 | 91.37 | 93.01 | 2.24 | 2.60 | 0.06 | 0.07 | 0.00 | 0.00 | 0.00 | 0.00 | (186) | (181) | 230 | 230 |
| 70(b) | 1.20 | 1.19 | 26.19 | 26.14 | 21.53 | 21.55 | 29.57 | 29.20 | 14.44 | 14.47 | 7.07 | 7.46 | 90 | 90 | 15 | 15 |
| 82 | 1.99 | 1.98 | 41.54 | 41.55 | 27.33 | 27.39 | 23.57 | 23.39 | 5.15 | 5.16 | 0.53 | 0.53 | 0 | (20) | 410 | 410 |
| 84 | 0.08 | 0.08 | 4.66 | 4.66 | 13.40 | 13.40 | 37.45 | 37.45 | 27.46 | 27.46 | 16.94 | 16.94 | 87 | 87 | " | " |
| 85 | 4.22 | 4.17 | 89.21 | 93.10 | 6.42 | 2.65 | 0.15 | 0.08 | 0.00 | 0.00 | 0.00 | 0.00 | (103) | (125) | " | " |
| 89(d) | 5.83 | 4.28 | 90.86 | 93.03 | 3.23 | 2.61 | 0.08 | 0.08 | 0.00 | 0.00 | 0.00 | 0.00 | 85 | 85 | " | " |

-continued

| Line No. | \multicolumn{2}{Compositions (Mol %) - Temperatures (°F.) - Pressures (psia)} | | | | | | | | | | | | |
|---|---|---|---|---|---|---|---|---|---|---|---|---|---|---|
| | $N_2$ | | $C_1$ | | $C_2$ | | $C_3$ | | $C_4$ | | $C_{5+}$ | | Temp. | | Press. | |
| | A | B | A | B | A | B | A | B | A | B | A | B | A | B | A | B |
| 95[e] | 0.00 | 0.00 | 1.16 | 1.22 | 33.03 | 40.60 | 38.75 | 35.54 | 18.04 | 15.06 | 9.02 | 7.58 | 90 | 90 | 405 | 405 |

[a] Lean Gas Feed
[b] Rich Gas Feed
[c] Plant Fuel Gas Products
[d] Pipeline Natural Gas Product
[e] Natural Gas Liquids Product While specific embodiments of the invention have been described for illustrative purposes, the invention is not to be limited thereto. Various other modifications or embodiments in the invention will be apparent to those skilled in the art in view of the disclosure. Such modifications and embodiments are within the spirit and scope of the present invention.

What is claimed is:

1. A process for cyrogenically separating a lean natural gas feed, containing a predominant amount of methane and a significant amount of nitrogen, and a separate rich natural gas feed, containing a predominant amount of ethane and higher molecular weight hydrocarbons; comprising, liquefying at least a portion of said lean gas feed, vaporizing at least a portion of said liquefied lean gas feed to produce a nitrogen-enriched gas product, and recovering a methane-enriched liquid product and an ethane and higher molecular weight hydrocarbon-enriched liquid product; and, simultaneously with said processing of said lean natural gas feed, liquefying at least a portion of said rich gas feed, vaporizing at least a portion of said liquefied rich gas feed and said ethane and higher molecular weight hydrocarbon-enriched liquid in a single vaporization step to produce a methane-enriched gas product, and recovering a natural gas liquids product.

2. A process in accordance with claim 1 wherein at least a portion of the energy necessary to liquefy the lean gas feed is provided by countercurrently passing at least a portion of the methane-enriched liquid product in indirect heat exchange with said lean gas feed.

3. A process in accordance with claim 2 wherein the methane-enriched gas product is combined with the methane-enriched liquid product prior to passing said methane-enriched liquid product in heat exchange with the lean gas feed.

4. A process in accordance with claim 1 wherein at least a portion of the energy necessary to liquefy the lean gas feed is provided by countercurrently passing at least a portion of the nitrogen-enriched gas product in indirect heat exchange with said lean gas feed.

5. A process in accordance with claim 4 wherein at least a second portion of the energy necessary to liquefy the lean gas feed is provided by cooling said lean gas feed by not more than about 40° F. with an external heat exchange medium.

6. A process in accordance with claim 1 wherein at least a portion of the energy necessary to liquefy the lean gas feed is provided by compressing the lean gas feed.

7. A process in accordance with claim 1 wherein at least a portion of the energy necessary to liquefy the lean gas feed is provided by countercurrently and separately passing at least a portion of the methane-enriched liquid product and at least a portion of the nitrogen-enriched gas product in indirect heat exchange with said lean gas feed.

8. A process in accordance with claim 1 wherein at least a portion of the energy necessary to vaporize the liquefied lean gas feed is provided by expanding said liquefied lean gas feed.

9. A process in accordance with claim 8 wherein the ethane and higher molecular weight hydrocarbon-enriched liquid is produced by separating a first portion of said ethane and higher molecular weight hydrocarbon-enriched liquid from the liquefied lean gas feed, prior to the expansion of said liquefied lean gas feed and separating the remainder of the ethane and higher molecular weight hydrocarbon-enriched liquid from the expanded lean gas feed.

10. A process in accordance with claim 9 wherein at least a portion of the expanded lean gas feed, remaining after the separation of the ethane and higher molecular weight hydrocarbon-enriched liquid, is at least partially reliquefied and said reliquefied remainder of the lean gas feed is at least partially vaporized to produce the methane-enriched liquid product and the nitrogen-enriched gas product.

11. A process in accordance with claim 10 wherein the energy necessary to reliquefy the remainder of the lean gas feed and at least a portion of the energy necessary to liquefy the lean gas feed, prior to the expansion of said lean gas feed, are provided by countercurrently passing at least a portion of the methane-enriched liquid product in indirect heat exchange with said remainder of said lean gas feed and said lean gas feed.

12. A process in accordance with claim 11 wherein the methane-enriched gas product is combined with the portion of the methane-enriched liquid product, after heat exchange of said portion of said methane-enriched liquid product with the remainder of the lean gas feed.

13. A process in accordance with claim 10 wherein the energy necessary to reliquefy the remainder of the lean gas feed and at least a portion of the energy necessary to liquefy the lean gas feed, prior to the expansion of said lean gas feed, are provided by countercurrently passing at least a portion of the nitrogen-enriched gas product in indirect heat exchange with said remainder of said lean gas feed and said lean gas feed.

14. A process in accordance with claim 10 wherein the energy necessary to reliquefy the remainder of the lean gas feed and at least a portion of the energy necessary to liquefy the lean gas feed, prior to the expansion of said lean gas feed, are provided by countercurrently and separately passing the methane-enriched liquid product and at least a portion of the nitrogen-enriched gas product in indirect heat exchange with said remainder of said lean gas feed and said lean gas feed.

15. A process in accordance with claim 14 wherein the methane-enriched gas product is combined with the portion of the methane-enriched liquid product, after heat exchange of said portion of said methane-enriched liquid product with the remainder of the lean gas feed.

16. A process in accordance with claim 8 wherein at least a portion of the methane-enriched liquid product is compressed.

17. A process in accordance with claim 16 wherein at least a portion of the energy necessary to compress the methane-enriched liquid product is provided by the expansion of the liquefied lean gas feed.

18. A process in accordance with claim 1 wherein at least a portion of the methane-enriched liquid product is countercurrently passed in indirect heat exchange with the nitrogen-enriched gas product to condense a portion of said nitrogen-enriched gas product and said condensed portion of said nitrogen-enriched gas product is countercurrently contacted with the vapors of the liquefied lean gas feed during the partial vaporization of said liquefied lean gas feed.

19. A process in accordance with claim 18 wherein at least a portion of the energy necessary to liquefy the lean gas feed is provided by countercurrently and separately passing the portion of the methane-enriched liquid product, after heat exchange with the nitrogen-enriched gas product, and the remainder of the methane-enriched liquid product in indirect heat exchange with said lean gas feed.

20. A process in accordance with claim 19 wherein the methane-enriched gas product is combined with the remainder of the methane-enriched liquid product prior to passing said remainder of said methane-enriched liquid product in heat exchange with the lean gas feed.

21. A process in accordance with claim 18 wherein at least a portion of the energy necessary to liquefy the lean gas feed is provided by countercurrently passing the uncondensed portion of the nitrogen-enriched gas product in indirect heat exchange with said lean gas feed.

22. A process in accordance with claim 21 wherein at least a second portion of the energy necessary to liquefy the lean gas feed is provided by cooling said lean gas feed by not more than about 40° F. with an external heat exchange medium.

23. A process in accordance with claim 18 wherein at least a portion of the energy necessary to liquefy the lean gas feed is provided by compressing the lean gas feed.

24. A process in accordance with claim 18 wherein at least a portion of the energy necessary to liquefy the lean gas feed is provided by countercurrently and separately passing the portion of the methane-enriched liquid product, the remainder of the methane-enriched liquid product and the uncondensed portion of the nitrogen-enriched gas product in indirect heat exchange with said lean gas feed.

25. A process in accordance with claim 18 wherein a portion of the energy necessary to vaporize the liquefied lean gas feed is provided by expanding said liquefied lean gas feed.

26. A process in accordance with claim 25 wherein the ethane and higher molecular weight hydrocarbon-enriched liquid product is produced by separating a first portion of said ethane and higher molecular weight hydrocarbon-enriched product from the liquefied lean gas feed, prior to the expansion of said liquefied lean gas feed, and separating the remainder of the ethane and higher molecular weight hydrocarbon-enriched product from the expanded lean gas feed.

27. A process in accordance with claim 26 wherein expanded lean gas feed, remaining, after the separation of the ethane and higher molecular weight hydrocarbon-enriched liquid product, is at least partially reliquefied and said reliquefied remainder of the lean gas feed is at least partially vaporized to produce the methane-enriched liquid product and the nitrogen-enriched gas product.

28. A process in accordance with claim 27 wherein the energy necessary to reliquefy the remainder of the lean gas feed and at least a portion of the energy necessary to liquefy the lean gas feed, prior to the expansion of said lean gas feed, are provided by countercurrently and separately passing the portion of the methane-enriched liquid product, after heat exchange with the nitrogen-enriched gas product, and the remainder of the methane-enriched liquid product in indirect heat exchange with said remainder of said lean gas feed and said lean gas feed.

29. A process in accordance with claim 28 wherein the methane-enriched gas product is combined with the portion of the methane-enriched liquid product, after heat exchange of said portion of said methane-enriched liquid product with the remainder of the lean gas feed.

30. A process in accordance with claim 27 wherein the energy necessary to reliquefy the remainder of the lean gas feed and at least a portion of the energy necessary to liquefy the lean gas feed, prior to the expansion of said lean gas feed, are provided by countercurrently passing the uncondensed portion of the nitrogen-enriched gas product in indirect heat exchange with said remainder of said lean gas feed and said lean gas feed.

31. A process in accordance with claim 27 wherein the energy necessary to reliquefy the remainder of the lean gas feed and at least a portion of the energy necessary to liquefy the lean gas feed, prior to the expansion of said lean gas feed, are provided by countercurrently and separately passing the portion of the methane-enriched liquid product, after heat exchange with the nitrogen-enriched gas product, the remainder of the methane-enriched liquid product and the uncondensed portion of the nitrogen-enriched gas product in indirect heat exchange with said remainder of said lean gas feed and said lean gas feed.

32. A process in accordance with claim 31 wherein the methane-enriched gas product is combined with the portion of the methane-enriched liquid product, after heat exchange of said portion of said methane-enriched liquid product with the remainder of the lean gas feed.

33. A process in accordance with claim 25 wherein at least a portion of the methane-enriched liquid product is compressed.

34. A process in accordance with claim 33 wherein at least a portion of the energy necessary to compress the portion of the methane-enriched liquid product is provided by the expansion of the liquefied lean gas feed.

35. A process in accordance with claim 1 wherein the ethane and higher molecular weight hydrocarbon-enriched liquid is countercurrently and directly contacted with the vapors of the rich gas feed during the vaporization of the said rich gas feed.

36. A process in accordance with claim 1 wherein at least a portion of the energy necessary to vaporize the liquefied lean gas feed is provided by expanding said liquefied lean gas feed, producing the ethane and higher molecular weight hydrocarbon-enriched liquid by separating a first portion of said ethane and higher molecular weight hydrocarbon-enriched liquid from said liquefied lean gas feed, prior to said expansion of said liquefied lean gas feed, and separating the remainder of the ethane and higher molecular weight hydrocarbon-enriched liquid from the expanded lean gas feed and said first portion of said ethane and higher molecular weight hydrocarbon-enriched liquid and said remainder of said ethane and higher molecular weight hydrocarbon-enriched liquid are sequentially, countercurrently and directly contacted with the vapors of the rich gas feed during the vaporization of said rich gas feed.

37. A process in accordance with claim 1 wherein the rich gas feed is separated into a vapor phase rich gas feed and a liquid phase rich gas feed and said vapor phase rich gas feed is countercurrently and directly contacted with the vapors from said liquid phase rich gas feed during the vaporization of said liquefied rich gas feed.

38. A process in accordance with claim 1 wherein the rich gas feed is separated into a first vapor phase rich gas feed and a first liquid phase rich gas feed, said first vapor phase rich gas feed is further separated into a second vapor phase rich gas feed and a second liquid phase rich gas feed, said first and second liquid phase rich gas feeds are combined and said second vapor phase rich gas feed is countercurrently and directly contacted with the vapors from said combined first and second liquid phase rich gas feeds during the vaporization of said combined rich gas feed.

39. A process in accordance with claim 38 wherein the first vapor phase rich gas feed is at least partially reliquefied, prior to the further separation of said first vapor phase rich gas feed.

* * * * *